United States Patent
Brown

(10) Patent No.: US 9,090,525 B2
(45) Date of Patent: Jul. 28, 2015

(54) PROCESS AND SYSTEM TO CONVERT METHANOL TO LIGHT OLEFIN, GASOLINE AND DISTILLATE

(75) Inventor: Stephen H. Brown, Annandale, NJ (US)

(73) Assignee: EXXONMOBIL RESEARCH AND ENGINEERING COMPANY, Annandale, NJ (US)

(*) Notice: Subject to any disclaimer, the term of this patent is extended or adjusted under 35 U.S.C. 154(b) by 684 days.

(21) Appl. No.: 12/891,257

(22) Filed: Sep. 27, 2010

(65) Prior Publication Data

US 2011/0152594 A1 Jun. 23, 2011

Related U.S. Application Data

(60) Provisional application No. 61/285,683, filed on Dec. 11, 2009.

(51) Int. Cl.
- *C07C 1/20* (2006.01)
- *C07C 9/14* (2006.01)
- *C07C 9/22* (2006.01)
- *C07C 2/12* (2006.01)
- *C10G 50/00* (2006.01)
- *C10G 3/00* (2006.01)

(52) U.S. Cl.
CPC ... *C07C 1/20* (2013.01); *C07C 2/12* (2013.01); *C10G 3/49* (2013.01); *C10G 3/54* (2013.01); *C10G 50/00* (2013.01); *C07C 2529/40* (2013.01); *C07C 2529/70* (2013.01); *C07C 2529/85* (2013.01); *C10G 2300/4081* (2013.01); *C10G 2400/02* (2013.01)

(58) Field of Classification Search
USPC ......... 585/310, 315, 319, 322, 324, 326, 327, 585/469, 638, 639, 640, 733
See application file for complete search history.

(56) References Cited

U.S. PATENT DOCUMENTS

| | | | | | |
|---|---|---|---|---|---|
| 4,150,062 | A | * | 4/1979 | Garwood et al. | 585/415 |
| 4,482,772 | A | * | 11/1984 | Tabak | 585/254 |
| 4,547,602 | A | * | 10/1985 | Tabak | 585/314 |
| 4,579,999 | A | * | 4/1986 | Gould et al. | 585/312 |

(Continued)

FOREIGN PATENT DOCUMENTS

| | | |
|---|---|---|
| WO | 2006076942 A1 | 7/2006 |
| WO | 2010097175 A1 | 9/2010 |

OTHER PUBLICATIONS

Heat Capacity Data, Heat Capacities of Propene, 1-Butene, 1-Pentene, and 1-Dodecene available at www.webbook.nist.gov, accessed on Sep. 20, 2014.*

(Continued)

*Primary Examiner* — In Suk Bullock
*Assistant Examiner* — Youngsul Jeong
(74) *Attorney, Agent, or Firm* — Glenn T. Barrett; David M. Weisberg

(57) ABSTRACT

The present invention provides a process for forming a refined hydrocarbon that includes providing a feed including methanol, dimethyl ether or a mixture thereof, and contacting the feed with a methanol conversion catalyst under suitable conditions to yield an intermediate composition including olefins having at least two carbon atoms. The intermediate composition is introduced to an oligomerization catalyst under suitable conditions to yield gasoline boiling range components and distillate boiling range components.

14 Claims, 1 Drawing Sheet

(56) References Cited

U.S. PATENT DOCUMENTS

| | | | |
|---|---|---|---|
| 4,689,205 A | | 8/1987 | Gould et al. |
| 4,788,369 A | * | 11/1988 | Marsh et al. .................. 585/408 |
| 4,830,635 A | * | 5/1989 | Harandi et al. ................. 44/449 |
| 4,898,717 A | | 2/1990 | Hsia et al. |
| 6,372,949 B1 | * | 4/2002 | Brown et al. ................. 585/639 |
| 2006/0199987 A1 | * | 9/2006 | Kuechler et al. ............. 585/502 |

OTHER PUBLICATIONS

PCT/US2010/058814, PCT International Search Report, Form PCT/ISA/210, dated Aug. 10, 2011, 5 pages.

PCT/US2010/058814, PCT Written Opinion of the International Searching Authority, Form PCT/ISA/237, dated Aug. 10, 2011, 5 pages.

\* cited by examiner

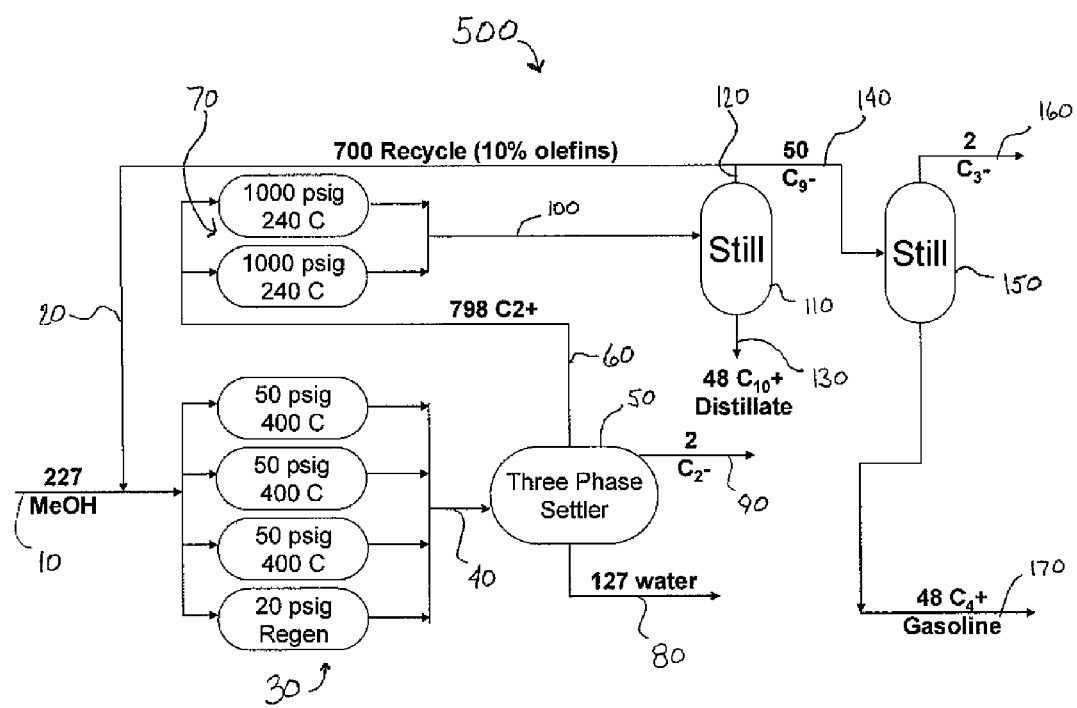

PROCESS AND SYSTEM TO CONVERT METHANOL TO LIGHT OLEFIN, GASOLINE AND DISTILLATE

CROSS REFERENCE TO RELATE APPLICATION

This application relates to and claims priority to U.S. Provisional Application No. 61/285,683, filed Dec. 11, 2009, entitled "Process and System to Convert Methanol To Light Olefin, Gasoline and Distillate."

FIELD OF THE INVENTION

The present invention relates to processes and systems that provide for the conversion of methanol and/or dimethylethers to light olefins, gasoline and/or distillate products.

BACKGROUND OF THE INVENTION

Aluminosilicate zeolite and other catalysts have been employed to convert methanol and/or dimethylethers to hydrocarbons, such as methanol to gasoline (MTG processes). The productivity of methanol conversion processes is limited primarily by the limits of the catalyst itself, which deactivates upon continued service due to, for example, the presence of steam, which in turn causes dealumination of the zeolite. The steaming conditions are inherent to a methanol and/or dimethylether conversion process and depend upon the total amount of methanol or oxygenate processed during the catalyst life, since one mole of water is generated for every mole of methanol or dimethylether converted.

MTG processes can generally yield, for example, between only 0.2 and 2 g hydrocarbon per g catalyst hour. As a result, catalyst costs are high.

Heat management is also a capital intensive endeavor, which is especially true in methanol conversion processes, such as MTG processes. Often, there is a need for large amounts of recycle solely to control heat, as the reaction from methanol to gasoline and distillate is highly exothermic. It is desirable to reduce the heat release in the first reaction stages in a MTG process.

In order to provide a methanol to gasoline process with increased economic feasibility, there is a need to improve the output of catalysts and to better manage the heat produced during the process in order to reduce heat recycle requirements.

SUMMARY OF THE INVENTION

The efficiency of a methanol to gasoline and distillate process is improved by selectively oligomerizing some, if not most, of the $C_5$– light olefins produced in a first methanol conversion reaction to a mixture of gasoline and distillate boiling range components in a second, integrated reactor. Moving light olefin oligomerization into a second reactor cuts the heat release in the first reactor significantly (e.g., by over 50%) and also improves catalyst output. As a result, inexpensive fixed bed adiabatic reactors can be used without large amounts of recycle to control heat. The second reaction can be conducted using proven, tubular reactor technology with no recycle streams.

Accordingly, one aspect of the present invention provides a process for forming a refined hydrocarbon that includes providing a feed including methanol, dimethyl ether or a mixture thereof, and contacting the feed with a methanol conversion catalyst under suitable conditions to yield an intermediate composition including olefins having at least two carbon atoms. The intermediate composition is introduced to an oligomerization catalyst under suitable conditions to yield gasoline boiling range components and distillate boiling range components. The process also includes separating the gasoline boiling range components and distillate boiling range components.

Another aspect of the present invention provides a system for forming a refined hydrocarbon that includes a feed including methanol, dimethyl ether or a mixture thereof, a first reaction vessel containing a methanol conversion catalyst in fluid communication with the feed, maintained under suitable conditions to yield an intermediate composition including olefins having at least two carbon atoms. The system also includes a second reaction vessel containing an oligomerization catalyst in fluid communication with the intermediate composition exiting the first reaction vessel. The second reaction vessel is maintained under suitable conditions to yield gasoline boiling range components and distillate boiling range components. The system further includes a separation assembly in fluid communication with the second reaction vessel to separate the gasoline boiling range components and distillate boiling range components exiting the second reaction vessel.

BRIEF DESCRIPTION OF THE DRAWINGS

The invention will now be described in conjunction with the accompanying drawings in which:

FIG. 1 is a process flow diagram of a prophetic and exemplary methanol to gasoline and distillate conversion process and system.

DETAILED DESCRIPTION OF THE INVENTION

Definitions

As used herein, the term "produced in an industrial scale" refers to a production scheme in which gasoline and/or distillate end products are produced on a continuous basis (with the exception of necessary outages for plant maintenance) over an extended period of time (e.g., over at least a week, or a month, or a year) with the expectation of generating revenues from the sale or distribution of the gas and/or distillate. Production at an industrial scale is distinguished from laboratory or pilot plant settings which are typically maintained only for the limited period of the experiment or investigation, and are conducted for research purposes and not with the expectation of generating revenue from the sale or distribution of the gasoline or distillate produced thereby.

As used herein, and unless specified otherwise, "gasoline" or "gasoline boiling range components" refers to a composition containing at least predominantly $C_5$-$C_{12}$ hydrocarbons. In one embodiment, gasoline or gasoline boiling range components is further defined to refer to a composition containing at least predominantly $C_5$-$C_{12}$ hydrocarbons and further having a boiling range of from about 100° F. to about 400° F. In an alternative embodiment, gasoline or gasoline boiling range components is defined to refer to a composition containing at least predominantly $C_5$-$C_{12}$ hydrocarbons, having a boiling range of from about 100° F. to about 400° F., and further defined to meet ASTM standard D439.

As used herein, and unless specified otherwise, the term "distillate" or "distillate boiling range components" refers to a composition containing predominately $C_{10}$-$C_{30}$ hydrocarbons. In one embodiment, distillate or distillate boiling range components is further defined to refer to a composition containing at least predominately $C_{10}$-$C_{30}$ hydrocarbons and further having a boiling range of from about 300° F. to about 700° F. Examples of distillates or distillate boiling range components include, but are not limited to, naphtha, jet fuel, diesel, kerosene, aviation gas, fuel oil, heating oil and blends thereof.

As used herein, and unless specified otherwise, the term "diesel" refers to middle distillate fuels containing at least predominantly $C_{10}$-$C_{25}$ hydrocarbons. In one embodiment, diesel is further defined to refer to a composition containing at least predominantly $C_{10}$-$C_{25}$ hydrocarbons, and further having a boiling range of from about 330° F. to about 700° F. In an alternative embodiment, diesel is as defined above to refer to a composition containing at least predominantly $C_{10}$-$C_{25}$ hydrocarbons, having a boiling range of from about 330° F. to about 700° F., and further defined to meet ASTM standard D975.

As used herein, the term "selective dimerization catalyst" refers to a catalyst, when introduced to olefins and aromatics under MOGD (Mobil Olefin to Gasoline/Distillate) operating conditions, that selectively oligomerizes olefins without alkylating the aromatics.

The selectivity of the selective dimerization catalyst can vary. In one embodiment, a selective dimerization catalyst oligomerizes (by alkylation of single ring aromatics in the feed with olefins) no more than 25 wt % of the aromatics in the feed. In another embodiment, a selective dimerization catalyst oligomerizes (by alkylation of single ring aromatics in the feed with olefins) no more than 10 wt % of the aromatics in the feed. In yet another embodiment, a selective dimerization catalyst oligomerizes (by alkylation of single ring aromatics in the feed with olefins) no more than 5 wt % of the aromatics in the feed.

As used herein, the term "selective distillate catalyst" refers to a catalyst, when introduced to olefins and aromatics under MOGD operating conditions, that oligomerizes both olefins and aromatics.

The selectivity of the selective distillate catalyst can vary. In one embodiment, a selective distillate catalyst oligomerizes (by alkylation of single ring aromatics in the feed with olefins) more than 50 wt % of the aromatics in the feed. In another embodiment, a selective distillate catalyst oligomerizes (by alkylation of single ring aromatics in the feed with olefins) more than 60 wt % of the aromatics in the feed. In yet another embodiment, a selective distillate catalyst oligomerizes (by alkylation of single ring aromatics in the feed with olefins) more than 70 wt % of the aromatics in the feed.

Reference will now be made to various aspects and embodiments of the disclosed subject matter in view of the definitions above. Reference to the systems will be made in conjunction with, and understood from, the method disclosed herein.

One aspect of the subject matter disclosed herein provides a process for forming a refined hydrocarbon that includes providing a feed including methanol, dimethyl ether or a mixture thereof, and contacting the feed with a methanol conversion catalyst under suitable conditions to yield an intermediate composition including olefins having at least two carbon atoms. The intermediate composition is introduced to an oligomerization catalyst under suitable conditions to yield gasoline boiling range components and distillate boiling range components. The process also includes separating the gasoline boiling range components and distillate boiling range components. In one embodiment, the gasoline and distillate components are produced in an industrial scale.

In one embodiment, separating the gasoline boiling range components and distillate boiling range components can include fractionating the gasoline boiling range components and distillate boiling range components in at least one distillation column. In alternative embodiments, separating the gasoline boiling range components and distillate boiling range components can include employing at least two distillation columns in series. In another embodiment, the first distillation column separates a $C_{10}^+$ distillate boiling range component and a $C_9^-$ overhead component, the second distillation column receiving the $C_9^-$ overhead component from the first distillation column and separating a $C_3^-$ overhead component and a $C_4^+$ gasoline boiling range component.

The process for forming a refined hydrocarbon can further include recycling a portion of the separated gasoline boiling range components containing an amount of $C_4$+ olefins (e.g., about 10% $C_4$+ olefins) to the feed to be contacted with the methanol conversion catalyst to yield $C_5$+ branched paraffins and $C_7$+ aromatics. Thus certain methods and systems described herein convert some of the gasoline range olefins (as opposed to $C_2$-$C_4$ olefins) to paraffins by selectively recycling $C_5$+ olefins to the methanol conversion reactor. This recycle serves at least two purposes: it controls the adiabatic temperature arise in the first reaction zone, and also converts $C_5$+ olefins to high octane $C_5$+ branched paraffins and $C_7$+ aromatics.

The amount of separated gasoline boiling range components containing $C_4$+ olefins that is recycled back to the methanol conversion reactor can be relatively high, as compared to the amount of methanol feed. In one embodiment the total amount of the recycle stream (which contains a portion of $C_5$+ olefins) is at least 50%, or at least 60%, or at least 70% of the total feed to the methanol conversion reactor. In another embodiment the recycle stream constitutes from about 20 to 95 wt %, or from about 40 to 90 wt %, or from about 50 to 75 wt % of the total feed to the methanol conversion reactor.

In one embodiment, the methanol conversion catalyst converts from about 90% to about 95%, or 99.9% of the methanol and dimethyl ether in the feed. Thus in certain embodiments, the process operates at a fixed partial methanol conversion and can recycle unconverted methanol by addition of appropriate hardware (e.g., a distillation column) In alternative embodiments, the methanol conversion is between about 80%, to about 99.9%, or between about 90% and 95%.

In certain embodiments that have partial methanol conversion, such partial conversion reduces heat released in the first reaction zone (i.e., the first methanol conversion stage), as compared to processes that run at 100% methanol conversion. Also the product of the methanol conversion, when run under partial methanol conversion conditions, have higher levels of olefins and lower levels of aromatics and paraffins, which again reduces the heat released.

In one embodiment, the process for forming a refined hydrocarbon further includes separating out $C_2^-$ gas and water from the intermediate composition after reaction with the methanol conversion catalyst. This separation can occur, for example, in a three phase settler apparatus. After the $C_2^-$ gas and water is separated from the intermediate composition, the liquid hydrocarbon product containing olefins having at least two carbon atoms can be directed to an oligomerization catalyst. The liquid hydrocarbon stream contains a large majority (e.g., above 90 wt %, or above 99 wt %) of the methanol conversion products. Because the product is mostly in the liquid phase, no compressors are required for further processing of the dissolved olefin products from methanol conversion.

In one embodiment, the methanol conversion catalyst is selected from ZSM-5 and ZSM-11 catalysts. In another embodiment, the methanol conversion catalyst is a ZSM-5 catalyst.

In one embodiment, the oligomerization catalyst is a selective dimerization catalyst and/or a selective distillate catalyst. The selective dimerization catalyst can be selected from ZSM-5, ZSM-57, ZSM-22, ZSM-48 and ZSM-12 catalysts. In one embodiment, the selective dimerization catalyst is a ZSM-5 catalyst. The selective distillate catalyst can be selected from MCM-22, zeolite beta-catalysts, FAU and ZSM-12 catalysts. In one embodiment, the selective distillate catalyst is an MCM-22 family catalyst. MCM (Mobil Catalytic Material) type catalysts are also known in the art, and can be obtained from, for example from ExxonMobil Catalyst Technologies LLC (Baytown, Tex.). MCM type catalysts, including synthesis details, are described in, for example, U.S. Pat. Nos. 7,198,711; 5,639,931; 5,296,428; 5,1460,29; and U.S. Published Application No. 2006/0194998. Each of these references are hereby incorporated by reference in their entirety.

In one embodiment, the methanol conversion catalyst is maintained in a first vessel maintained at a temperature of from about 300° C. to about 450° C. and a pressure of about 100 to about 400 psia. The vessel containing the methanol conversion catalyst can be a fixed bed adiabatic reactor.

In one embodiment, the oligomerization catalyst is maintained in a second vessel maintained at a temperature of from about 150° C. to about 300° C. and a pressure of about 600 to about 2000 psia. The vessel containing the oligomerization catalyst can be a fixed bed adiabatic reactor. Alternatively, the vessel containing the oligomerization catalyst can be an isothermal tubular reactor.

Another aspect of the present invention provides a system for forming a refined hydrocarbon that includes a feed including methanol, dimethyl ether or a mixture thereof, a first reaction vessel containing a methanol conversion catalyst in fluid communication with the feed, maintained under suitable conditions to yield an intermediate composition including olefins having at least two carbon atoms. Methanol conversion is conducted in standard reactor vessels 30. Catalyst activity, selectivity, and stability are relatively independent of temperature making the process well-suited to operation in a simple, adiabatic fixed-bed reactor. Such a reactor is comprised of a cylinder with support grids to prevent solids from leaving the entrance and exit. Inert spheres (e.g. alumina spheres) having a diameter of 1 to 100 mm are typically placed on top of the support screen at the bottom of the reactor at a depth of between 6 inches to 3 feet. 0.25 to 3 mm extrudates are poured on top of the spheres. The reaction is 100% gas phase so distribution of feed and catalyst is not a concern.

The effluent from the methanol conversion reactor is maintained at full reaction pressure (e.g., 50 psig), and cooled to near room temperature to maximize condensation. The effluent condenses into three phases: liquid water, liquid hydrocarbon, and gas. A simple means of separating the three phases is to run the condensed product into a large, cylindrical tank 50 held near room temperature and 50 psig. The vessel is sized to hold 1 to 10 hours worth of reactor product. It is contemplated that both larger and smaller vessels may be used. The product readily separates into gas at the top of the vessel, a liquid hydrocarbon phase with a density of close to 0.65 g/cc in the middle of the vessel, and a 1.0 g/cc water phase at the bottom of the vessel. Piping and pumps are used to maintain steady state levels of water and hydrocarbon phase in the vessel. The gas phase is pushed out of piping 60 exiting the top of the vessel 50 by the pressure of the vessel. Pressure in the vessel is maintained by continuously bleeding the product gasses.

The hydrocarbon liquid is pumped using any of a variety of liquid pumps up to the reaction pressure required for oligomerization (e.g., 1000 psig). The pressurized liquid is heated to reaction temperature (e.g., 240° C.) and fed to the oligomerization reactor 70. The system also includes a second reaction vessel or oligomerization reactor containing an oligomerization catalyst in fluid communication with the intermediate composition exiting the first reaction vessel, the second reaction vessel maintained under suitable conditions to yield gasoline boiling range components and distillate boiling range components. Catalyst activity, selectivity, and stability are a function of temperature in the olefin oligomerization reactor and isothermal operation is preferred. Therefore the preferred reactor design is a tubular reactor. A preferred reactor consists of multiple straight tubes between 1 and 3 inches in diameter packed into a cylindrical shell between two tube sheets. The reactors are disclosed in greater detail in copending U.S. patent application Ser. No. 11/140,853, to Brown et al, entitled "Reactor Temperature Control", the disclosure of which is hereby incorporated in its entirety by reference. Catalyst extrudates between 0.5 and 3 mm are poured into the tubes. Water/steam is circulated through the shell to remove the heat of reaction. The reactor effluent is depressured to between 100 and 600 psig to feed a series of distillation columns that separates the product into C3−, C4+ gasoline, and C10+ distillate products. Part of the C4+ gasoline is recycled 20.

The system further includes a separation assembly 50, described above, in fluid communication with the second reaction vessel to separate the gasoline boiling range components and distillate boiling range components exiting the second reaction vessel. The separation assembly can include a three phase settler apparatus in fluid communication with the first reaction vessel and the second reaction vessel.

Exemplary further embodiments of the present invention are provided below for illustrative purposes, and not for purposes of limitation.

An exemplary methanol to gasoline and distillate conversion system and process (500) is shown in FIG. 1. A feed stream (10) containing 227 units of methanol are added to a recycle stream (20) containing 700 units of $C_4+$ gasoline product that is recycled to the methanol conversion reactors (30). In this particular embodiment, three methanol conversion reactors each containing ZSM-5 catalysts are maintained at 50 psig and 400° C. A fourth methanol conversion reactor is devoted to catalyst regeneration and is not placed online. The conversion reactor that is undergoing regeneration is maintained at 20 psig and about 510° C. The feedstocks are preheated to between 330° C. and 370° C. by means of a heat exchanger or other appropriate hardware (not shown). The reaction exotherm increases the reactor temperature by about 30° C. At the start of cycle, the feed is preheated to 330° C. and the WHSV (weight hourly space velocity) is adjusted to achieve about 99% methanol conversion. During the course of the run, the feed preheat temperature is increased and the feed WHSV is decreased in order to maintain a constant 99% methanol conversion.

The total reactor product (40) is cooled to near 40° C. by a heat exchanger (not shown) or other appropriate device, and the pressure is maintained at 50 psig. Most of the product is the $C_4+$ isoparaffins and aromatics that dominate the gasoline product composition. Since recycle gasoline comprises most of the feed to the reactor, and most of the composition is unreactive at methanol conversion conditions, most of the product is unconverted gasoline feedstock molecules. The large amount of gasoline range product is sufficient to dissolve the relatively small quantity of $C_3-$ product from methanol conversion. The reactor product (40) is fed to a three phase settler apparatus (50). The reactor product splits into three phases—water (80), liquid hydrocarbon (60), and $C_2$– gasses (90). At these conditions, the liquid hydrocarbon (60) contains >95 wt % of the methanol conversion products. Because the product is mostly in the liquid phase, no compressors are required for further processing of the dissolved olefin products from methanol conversion.

The liquid hydrocarbon phase stream (60) exiting the three-phase settler apparatus is pumped to 1000 psig by means of a feed pump (not shown) or other suitable apparatus and passed through an oligomerization reactor (70) that operates with a start cycle temperature of about 200° C. and an end cycle temperature of near 300° C. The oligomerization reactor itself (i.e. the second reactor vessel) is maintained at about 1000 psig and 200-300° C., and contains a MCM-22 catalyst and/or a ZSM-5 catalyst depending on, among other things, the desired aromatics content of the distillate (preferably jet fuel), as discussed below. The oligomerization reactor is adjusted to maintain constant $C_4^-$ olefin conversion between about 85 and 95%.

Simple fixed bed reactors can be used, since the large recycle stream (20) of mostly unreacted gasoline range molecules which limits the adiabatic temperature rise. Alternatively, isothermal tubular reactors can be used.

The oligomerization reactor product stream (100) is fed to a first still or distillation column (110) maintained under suitable conditions to separate primarily gasoline-boiling range overhead components (including 10% olefins) (120), and $C_{10}+$ distillate boiling range components (130). The gasoline-boiling range components is split into two streams: the first stream (20) is recycled back to the methanol conversion reaction and the second stream (140) forms the feed for the second still or distillation column (150). The second still is maintained under suitable conditions to separate the relatively small amounts of $C_4^-$ overhead components (160) from the $C_4+$ gasoline components (170). The gasoline product (170) can be fractionated between 1,2,4 trimethylbenzene and durene in order to control the durene content of the resulting gasoline.

As noted above, the oligomerization catalyst can be a selective dimerization catalyst (e.g., ZSM-5) and/or a selective distillate catalyst (e.g., MCM-22), or a mixture of both types of catalysts. The selective dimerization catalyst selectively oligomerizes olefins without alkylating the aromatics in the feed (60). The selective distillate catalyst oligomerizes both olefins and aromatics. The ratio of selective dimerization catalyst (e.g., ZSM-5) and selective distillate catalyst (e.g., MCM-22) can be adjusted to control the aromatics content of the product distillate. If a selective dimerization catalyst is used in higher amounts, the process produces more gasoline. Employing a selective distillate catalyst in the vessel containing the oligomerization catalyst will add side chains to single ring polymethylaromatics, shifting the boiling point of the molecules from the gasoline boiling range to the distillate boiling range. Thus, if a selective distillate catalyst is employed, the process produces more distillate and less gasoline.

Catalysts

Although ZSM-5 and MCM-22 catalysts are described above, the process and systems of the present application are not limited thereto. Other catalysts, including the catalysts mentioned below can be used in the process of the present invention as methanol conversion catalyst and/or the oligomerization catalyst. The methanol conversion catalyst and the oligomerization catalyst can be the same or different.

As disclosed in U.S. Pat. No. 7,361,798, which is hereby incorporated in its entirety by reference herein, zeolites are classified by the Structure Commission of the International Zeolite Association according to the rules of the IUPAC Commission on Zeolite Nomenclature. A framework-type describes the topology and connectivity of the tetrahedrally coordinated atoms constituting the framework and makes an abstraction of the specific properties for those materials. Molecular sieves for which a structure has been established are assigned a three letter code and are described in the Atlas of Zeolite Framework Types, $5^{th}$ edition, Elsevier, London, England (2001), which is incorporated in its entirety by reference herein.

Examples of aluminosilicate zeolite catalyst that can be included in the process and systems of the present invention include, but are not limited to, ZSM-5, ZSM-11, ZSM-12, ZSM-22, ZSM-23, ZSM-35, ZSM-48, ZSM-50, ZSM-57 and mordenite, MCM-22, MCM-36, MCM-49, MCM-56, MCM-65, MCM-68, MCM-71 and ITQ-13.

In one embodiment, the catalyst is a ZSM-type catalyst. ZSM (Zeolite Socony Mobil) catalysts are known in the art and can be commercially obtained or synthesized. Commercially available ZSM-type catalysts can be obtained from, for example, Zeolyst International Corporation (Valley Forge, Pa.), BASF Catalysts LLC (Iselin, N.J.), Sud-Chemie Incorporated (Louisville, Ky.), and, preferably, from ExxonMobil Catalyst Technologies LLC (Baytown, Tex.). ZSM catalysts, including synthesis details, are generally described, for example, in U.S. Pat. Nos. 5,367,100; 4,845,063; 4,872,968; 4,076,842; 4,046,859; 4,035,430; 4,021,331; 4,016,245; 3,972,983; 3,965,205; 3,832,449; 3,709,979; 3,702,886; 3,303,069; and Re. 28,341. The contents of each of these patents are hereby incorporated by reference in its entirety.

In another embodiment, the methanol conversion catalyst and/or oligomerization catalyst is selected from ZSM-5, ZSM-11, ZSM-12, ZSM-22, ZSM-23, ZSM-35, ZSM-48, ZSM-50, ZSM-57 catalysts.

In yet another embodiment, the methanol conversion catalyst and/or oligomerization catalyst is an MCM (Mobil Catalytic Material) type catalysts. MCM catalysts are also known in the art, and can be obtained from, for example from ExxonMobil Catalyst Technologies LLC (Baytown, Tex.). MCM type catalysts, including synthesis details, are described in, for example, U.S. Pat. Nos. 7,198,711; 5,639,931; 5,296,428; and 5,146,029; and U.S. Published Application No. 2006/0194998. Each of these references is hereby incorporated by reference in their entirety.

In a still further embodiment, the methanol conversion catalyst and/or oligomerization catalyst is a zeolite beta catalyst. Zeolite beta catalysts are known in the art and can be obtained from ExxonMobil Catalyst Technologies LLC (Baytown, Tex.). Zeolite beta catalysts, including synthesis details, are described in, for example, U.S. Pat. Nos. 5,457,078; 5,232,579 and 5,710,085; and U.S. Published Application No. 2008/0261803. Each of these references are hereby incorporated by reference in their entirety.

In another embodiment, the methanol conversion catalyst and/or oligomerization catalyst is a FAU-type catalyst. FAU-type catalysts are known in the art and can be obtained from ExxonMobil Catalyst Technologies LLC (Baytown, Tex.). FAU-type catalysts, including synthesis details, are described in, for example, U.S. Pat. Nos. 5,536,483; 6,221,324; 6,350,428; and U.S. Published Application No. 2008/0161619. Each of these references is hereby incorporated by reference in its entirety.

In yet another embodiment, the methanol conversion catalyst and/or oligomerization catalyst is selected from MCM-22, MCM-36, MCM-49, MCM-56, MCM-65, MCM-68 and MCM-71 catalysts.

In an alternative embodiment, the methanol conversion catalyst and/or oligomerization catalyst is an ITQ type catalysts. ITQ type catalysts, including synthesis details, are described in, for example, U.S. Pat. Nos. 7,449,169; 7,081,556; 6,709,572; and 6,469,226, as well as published U.S. Application No. 2008/0021253. Each of these references is hereby incorporated by reference in its entirety.

In another embodiment, the ITQ type catalyst is ITQ-13. ITQ-13 structure is 10×10×9-member rings. Pore sizes of the ITQ-13 are 4.8×5.3 A; 4.8×5.1 A; 4.0×4.8 A (9-member ring).

Other molecular sieves catalysts that can be used as the methanol conversion catalyst and/or oligomerization catalyst. These catalysts include those described in R. Szostak, Handbook of Molecular Sieves, Van Nostrand Reinhold, New York, N.Y. (1992), which is hereby incorporated by reference in its entirety.

Other suitable catalysts, particularly methanol conversion catalysts, are disclosed in U.S. Pat. No. 6,673,978, which is hereby incorporated by reference in its entirety. These catalysts include, for example, silcoaluminophosphate (SAPO) molecular sieve catalysts having a $Si/Al_2$ ratio of less than 0.65 and an average pore size ranging from 3.5 angstroms to 4.2 angstroms. The SAPO catalysts can be substituted with alkali metal ions (Group IA), alkaline earth metal ions (Group IIA), rare earth ions (Group IIIB) and the additional transition cations of Groups IVB, VB, VIIB, VIIB, VIIIB, and IB.

Methanol to Olefin Reaction Conditions

As noted above, embodiments of the presently disclosed subject matter include a stage in which methanol, dimethyl ether, or a mixture thereof is introduced to a methanol conversion catalyst under suitable conditions to yield a light $C_2+$ olefin composition. This process is known as a MTO (methanol to olefin) reaction.

MTO reaction conditions are known in the art. For example, U.S. Pat. No. 6,673,978 discloses MTO reaction conditions. In one embodiment, the weight hourly space velocity (WHSV) of methanol and dimethyl ether feed stock ranges from about 0.1 $hr^{-1}$ to about 500 $hr^{-1}$, or from about 0.5 $hr^{-1}$ to about 100 $hr^{-1}$, or from about 1 $hr^{-1}$ to about 10 $hr^{-1}$, or from about 2 $hr^{-1}$ to about 5 $hr^{-1}$.

In one embodiment, the temperature of the reaction vessel containing the methanol conversion catalyst ranges from about 250° C. to about 600° C., or from about 300° C. to about 500° C., or from about 330° C. to about 430° C. (e.g., about 380° C.). In another embodiment, the reaction pressure of the reaction vessel containing the methanol conversion catalyst ranges from about 5 psig to about 500 psig, or from about 10 psig to about 200 psig, or from about 25 psig to about 75 psig (e.g., 50 psig).

Olefin to Gasoline/Distillate Reaction Conditions

Certain processes disclosed herein also include a stage in which a light $C_2+$ olefin composition is contacted with an oligomerization catalyst and converted to gasoline and distillate. This process is known as a MOGD or MOG/D (Mobil Olefin to Gasoline/Distillate) reaction.

MOGD reaction conditions are known in the art. For example, U.S. Pat. No. 4,720,600, which is hereby incorporated by reference in its entirety, discloses MOGD reaction conditions. In one embodiment, the WHSV of olefin feed to the reaction vessel containing the oligomerization catalyst ranges from about 0.1 to about 4 $hr^{-1}$, or from about 0.3 to about 3 $hr^{-1}$, or from about 0.5 to about 2.0 $hr^{-1}$, or from about 0.6 to about 1.0 $hr^{-1}$.

In one embodiment, the temperature of the reaction vessel containing the oligomerization catalyst ranges from about 100° C. to about 350° C., or from about 150° C. to about 350° C., or from about 200° C. to about 300° C. (e.g., about 240° C.). In another embodiment, the reaction pressure of the reaction vessel containing the oligomerization catalyst ranges from about 500 psig to about 3000 psig, or from about 600 psig to about 2500 psig, or from about 800 psig to about 1500 psig (e.g., 1000 psig). In yet another embodiment, the reaction temperature is increased to maintain 85-95% conversion of the propylene plus butenes in the feedstock. Over time, the catalyst deactivates. Increasing the reaction temperature offsets the decline in catalyst activity.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of each of which is incorporated herein by reference in its entirety for all purposes.

The invention claimed is:

1. A process for converting a feed comprising methanol to a hydrocarbon product, comprising:
    (a) contacting the feed in a first, fixed bed adiabatic conversion reactor with a methanol conversion catalyst under suitable conditions to yield an intermediate composition including olefins having at least two carbon atoms;
    (b) separating a liquid hydrocarbon phase comprising recycled gasoline boiling range components unreacted in the first reactor and methanol conversion products from the $C_{2-}$ gas and water in the intermediate composition,
    (c) introducing the liquid hydrocarbon phase from separation step (b) to a second, separate conversion reactor containing an olefin oligomerization catalyst under suitable conditions to yield gasoline boiling range components and distillate boiling range components;
    (d) separating the gasoline boiling range components and distillate boiling range components; and
    (e) recycling a portion of the separated gasoline boiling range components containing at least predominantly $C_5$ to $C_{12}$ hydrocarbons to the feed to be contacted with the methanol conversion catalyst in the first conversion reactor in an amount which constitutes from about 40 to about 90 wt % of the total feed to the methanol conversion catalyst to control the adiabatic temperature arise in the first conversion reactor and convert $C_{5+}$ olefins in the recycle stream to $C_{5+}$ branched paraffins and $C_{7+}$ aromatics.

2. The process of claim 1, wherein the methanol conversion catalyst converts from about 90% to about 95% of the methanol in the feed.

3. The process of claim 1, wherein the separation of the $C_{2-}$ gas and water from the intermediate composition occurs in a three phase settler apparatus.

4. The process of claim 1, wherein separating the gasoline boiling range components and distillate boiling range components includes fractionating the gasoline boiling range components and distillate boiling range components in at least one distillation column.

5. The process of claim 4, wherein at least two distillation columns are employed in series, the first distillation column separating a $C_{10+}$ distillate boiling range component and a $C_{9-}$ overhead component, the second distillation column receiving the $C_{9-}$ overhead component from the first distillation column and separating a $C_{3-}$ overhead component and $C_{4+}$ gasoline boiling range component.

6. The process of claim 1, wherein the methanol conversion catalyst is selected from ZSM-5, ZSM-11, MCM-68 and ZSM-12 catalysts.

7. The process of claim 6, wherein the methanol conversion catalyst is a ZSM-5 catalyst.

8. The process of claim 1, wherein the olefin oligomerization catalyst is a selective dimerization catalyst selected from ZSM-5, ZSM-57, ZSM-22, ZSM-12, ZSM-48 and SAPO-11 catalysts.

9. The process of claim 8, wherein the olefin oligomerization catalyst is a ZSM-5 catalyst.

10. The process of claim 1, wherein the olefin oligomerization catalyst is a selective distillate catalyst selected from MCM-22, zeolite beta-catalysts, FAU and ZSM-12 catalysts.

11. The process of claim 1, wherein the methanol conversion catalyst is maintained in a first vessel maintained at a temperature of from about 330° C. to about 430° C. and a pressure of about 15 psig to about 75 psig.

12. The process of claim 1, wherein the olefin oligomerization catalyst is maintained in a second vessel maintained at a temperature of from about 200° C. to about 300° C. and a pressure of from about 750 psig to about 1500 psig.

13. The process of claim 1 in which the liquid hydrocarbon phase separated in step (b) comprises greater than 95 wt % of the methanol conversion products from the first reactor.

14. The process of claim 1 in which the liquid hydrocarbon phase separated in step (b) is introduced into the second reactor with no compression.

* * * * *